United States Patent [19]

Schmidt et al.

[11] 4,312,664

[45] Jan. 26, 1982

[54] COMPOSITIONS AND METHODS FOR IMPROVING THE TOLERANCE BY CROP PLANTS OF HERBICIDALLY ACTIVE ACETANILIDES

[75] Inventors: Robert R. Schmidt, Cologne; Wilfried Faust, Odenthal, both of Fed. Rep. of Germany

[73] Assignee: Bayer Aktiengesellschaft, Leverkusen, Fed. Rep. of Germany

[21] Appl. No.: 45,371

[22] Filed: Jun. 4, 1979

[30] Foreign Application Priority Data

Jun. 28, 1978 [DE] Fed. Rep. of Germany ....... 2828303

[51] Int. Cl.³ .................... C07D 231/02; A01N 9/02; A01N 9/22
[52] U.S. Cl. .......................... 71/92; 71/95; 71/98; 71/97; 71/118; 71/90; 548/107; 548/128; 548/143; 548/253; 548/252; 548/255; 548/262; 564/202
[58] Field of Search ............................................. 71/92

[56] References Cited

U.S. PATENT DOCUMENTS

| | | | |
|---|---|---|---|
| 3,769,301 | 10/1973 | Olin | 71/95 |
| 3,907,544 | 9/1975 | Olin | 71/93 |
| 4,055,410 | 10/1977 | Cheng | 71/92 |
| 4,104,051 | 8/1978 | Cheng | 71/92 |

*Primary Examiner*—Donald G. Daus
*Assistant Examiner*—James H. Turnipseed
*Attorney, Agent, or Firm*—Sprung, Felfe, Horn, Lynch & Kramer

[57] ABSTRACT

Novel herbicidal composition comprising
 (1) a herbicidally active acetanilide and
 (2) as an antidote against damage to crop plants, N,N-dially-dichloroacetamide of the formula

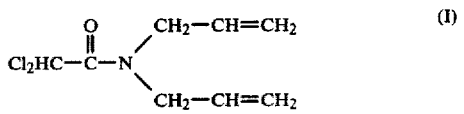

15 Claims, No Drawings

COMPOSITIONS AND METHODS FOR IMPROVING THE TOLERANCE BY CROP PLANTS OF HERBICIDALLY ACTIVE ACETANILIDES

The present invention relates to compositions and methods for improving the tolerance by crop plants to certain herbicidally active acetanilides. More specifically, these methods involve the use of N,N-diallyldichloroacetamide as an antidote for improving said tolerance. The present invention also relates to new active-compound combinations which comprise N,N-diallyldichloroacetamide and certain acetanilides and which have particularly good selective herbicidal properties.

In the present context, by "antidotes" ("safeners") there are to be understood substances which are capable of specific antagonization of harmful actions of herbicides on crop plants, that is to say which are capable of protecting crop plants without thereby noticeably influencing the herbicidal action on the weeds to be combated.

It is known that when certain acetanilides are used for combating weeds in corn and other crops, they cause damage, to a greater or lesser extent, to the crop plants.

It is furthermore known that N,N-diallyldichloroacetamide is suitable for preventing damage to crop plants by certain herbicidal active compounds, in particular thiolcarbamates (see DE-OS (German Published Specification) No. 2,218,097). However, the applicability of this substance as an antidote depends to a certain extent on the particular herbicidal active compound.

It has now been found that N,N-diallyl-dichloroacetamide, of the formula

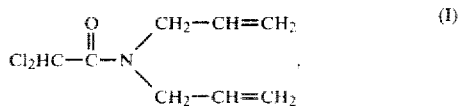

is outstandingly suitable as an antidote for improving the tolerance by crop plants of herbicidally active acetanilides of the general formula

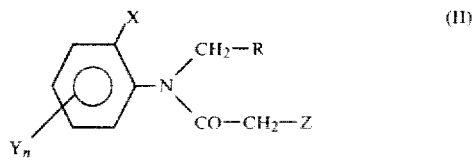

in which
R represents an optionally substituted N-containing heterocyclic radical,
X and Y, which may be identical or different, each represent alkyl,
Z represents halogen and
n represents 0, 1 or 2,
and herbicidally active acid-addition salts and metal salt complexes thereof, or of the general formula

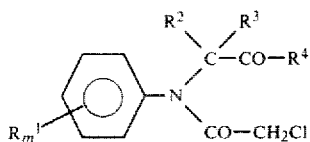

in which
$R^1$ represents alkyl, halogen, halogenoalkyl, alkylthio, alkylsulphonyl, aminosulphonyl, cyano or nitro,
$R^2$ and $R^3$, which may be identical or different, each represent hydrogen, alkyl, halogen, halogenoalkyl or optionally substituted phenyl,
$R^4$ represents alkyl or optionally substituted phenyl and
m represents 0, 1, 2, 3, 4 or 5,
or of the general formula

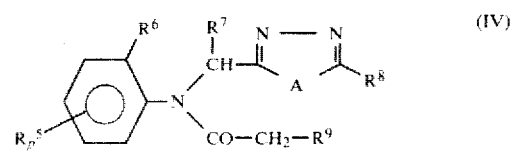

in which
A represents oxygen, sulphur or the grouping $>NR^{10}$,
$R^7$ represents hydrogen or alkyl,
$R^8$ represents hydrogen, alkyl, halogenoalkyl, alkenyl, alkynyl, cycloalkyl, halogen, optionally substituted aryl, optionally substituted aralkyl or the grouping $-OR^{11}$, $-SR^{11}$ or $NR^{10}R^{11}$,
$R^{10}$ represents hydrogen, alkyl or optionally substituted aryl,
$R^{11}$ represents hydrogen, alkyl, halogenoalkyl, alkenyl, alkynyl, cycloalkyl or optionally substituted aralkyl,
$R^5$ represents alkyl,
$R^6$ represents alkyl or halogen,
$R^9$ represents halogen and
p represents 0, 1 or 2.

Accordingly, the present invention provides a herbicidal composition comprising (1), as active ingredient, at least one compound selected from acetanilides of the formula (II), acid-addition salts and metal salt complexes thereof, acetanilides of the formula (III) and acetanilides of the formula (IV), and (2), as an antidote against damage to crop plants, the compound of the formula (I), alone or in admixture with a diluent or carrier.

The invention also provides a method of protecting crop plants against damage by a herbicidally active compound selected from acetanilides of the formula (II), acid-addition salts and metal salt complexes thereof, acetanilides of the formula (III) and acetanilides of the formula (IV), which method comprises applying to the crop plants, or to a habitat thereof, the compound of the formula (I) alone or in admixture with a diluent or carrier.

Preferred acetanilides of the formula (II) are those in which R represents a pyrazol-1-yl, imidazol-1-yl, 1,2,4-triazol-1-yl, 1,2,3-triazol-1-yl, 1,3,4-triazol-1yl, 1,2,3,4-tetrazol-1-yl or pyrrol-1-yl radical which is optionally substituted, the preferred substituents being halogen (especially fluorine, chlorine or bromine) and alkyl with 1 to 4 carbon atoms;

X and Y, which may be identical or different, each represent straight-chain or branched alkyl with 1 to 4 carbon atoms; and Z represents chlorine or bromine.

Preferred acetanilides of the formula (III) are those in which $R^1$ represents straight-chain or branched alkyl with 1 to 6 (especially 1 to 4) carbon atoms, fluorine, chlorine, bromine, halogenoalkyl with up to 3 carbon atoms and up to 5 identical or different halogen atoms (preferred halogens being fluorine and chlorine and trifluoromethyl being mentioned as an example), alkylthio with 1 to 4 carbon atoms, alkylsulphonyl with 1 to 4 carbon atoms, aminosulphonyl, cyano or nitro;

$R^2$ and $R^3$, which may be identical or different, each represent hydrogen, straight-chain or branched alkyl with 1 to 4 carbon atoms, fluorine, chlorine, bromine, halogenoalkyl with up to 3 carbon atoms and up to 5 identical or different halogen atoms (preferred halogens being fluorine and chlorine) or phenyl which is optionally monosubstituted or polysubstituted, the preferred substituents being alkyl with 1 to 6(especially 1 to 4) carbon atoms, fluorine, chlorine, bromine, halogenoalkyl with up to 3 carbon atoms and up to 5 identical or different halogen atoms (preferred halogens being fluorine and chlorine and trifluoromethyl being mentioned as an example), alkylthio with 1 to 4 carbon atoms, alkylsulphonyl with 1 to 4 carbon atoms, aminosulphonyl, cyano and nitro;

$R^4$ represents straight-chain or branched alkyl with 1 to 6 (especially 1 to 4) carbon atoms or phenyl which is optionally monosubstituted or polysubstituted, the preferred substituents being alkyl with 1 to 6 (especially 1 to 4) carbon atoms, fluorine, chlorine, bromine, halogenoalkyl with up to 3 carbon atoms and up to 5 identical or different halogen atoms (preferred halogens being fluorine and chlorine and trifluoromethyl being mentioned as an example), alkylthio with 1 to 4 carbon atoms, alkylsulphonyl with 1 to 4 carbon atoms, amino-sulphonyl, cyano, nitro, phenyl and phenoxy, which last two substituents can themselves also be substituted by alkyl with 1 to 6 (especially 1 to 4) carbon atoms, fluorine, chlorine, bromine, halogenoalkyl with up to 3 carbon atoms and up to 5 identical or different halogen atoms (preferred halogens being fluorine and chlorine and trifluoromethyl being mentioned as an example ), alkylthio with 1 to 4 carbon atoms, alkylsulphonyl with 1 to 4 carbon atoms, aminosulphonyl, cyano, or nitro.

Preferred acetanilides of the formula (IV) are those in which A represents oxygen, sulphur or the grouping $>NR^{10}$, wherein $R^{10}$ represents hydrogen, straight-chain or branched alkyl with 1 to 4 carbon atoms or aryl with 6 to 10 carbon atoms (especially phenyl), it being possible for the aryl radical to carry one or more substituents selected from halogen, alkyl with 1 to 4 carbon atoms, alkoxy with 1 to 2 carbon atoms, alkylthio with 1 or 2 carbon atoms, cyano, nitro and halogenoalkyl with up to 2 carbon atoms and up to 5 identical or different halogen atoms (halogens which may be mentioned 60 being, in particular, fluorine and chlorine);

$R^7$ represents hydrogen or methyl;

$R^8$ represents hydrogen, straight-chain or branched alkyl with 1 to 4 carbon atoms, halogenoalkyl with up to 3 carbon atoms and up to 5 identical or different halogen atoms (preferred halogens being fluorine and chlorine and trifluoromethyl being mentioned as an example), alkenyl or alkynyl with in either case 2 to 4 carbon atoms, cycloalkyl with 5 to 7 carbon atoms, fluorine, chlorine, bromine or aryl with 6 to 10 carbon atoms (especially phenyl), it being possible for the aryl radical to carry one or more substituents selected from halogen, alkyl with 1 to 4 carbon atoms, alkoxy with 1 or 2 carbon atoms, alkylthio with 1 or 2 carbon atoms, cyano, nitro and halogenoalkyl with up to 2 carbon atoms and up to 5 identical or different halogen atoms (preferred halogens being fluorine or chlorine and trifluoromethyl being mentioned as a specific example of halogenoalkyl), or $R^8$ represents aralkyl with 6 to 10 atoms in the aryl part and 1 to 4 carbon atoms in the alkyl part (especially benzyl), it being possible for the aralkyl radical to carry one or more substituents in the aryl part selected from halogen, alkyl with 1 to 4 carbon atoms, alkoxy with 1 or 2 carbon atoms, alkylthio with 1 or 2 carbon atoms, cyano, nitro and halogenoalkyl with up to 2 carbon atoms and up to 5 identical or different halogen atoms (preferred halogens being fluorine and chlorine and trifluoromethyl being mentioned as a specific example of halogenoalkyl), or $R^8$ represents the grouping $—OR^{11}$, $—SR^{11}$ or $—NR^{10}R^{11}$, wherein $R^{10}$ represents hydrogen, straight-chain or branched alkyl with 1 to 4 carbon atoms or aryl with 6 to 10 carbon atoms (especially phenyl), it being possible for the aryl radical to carry one or more substituents selected from halogen, alkyl with 1 to 4 carbon atoms, alkoxy with 1 or 2 carbon atoms, alkylthio with 1 or 2 carbon atoms, cyano, nitro and halogenoalkyl with up to 2 carbon atoms and up to 5 identical or different halogen atoms (halogens which may be mentioned being, in particular, fluorine and chlorine) and $R^{11}$ represents hydrogen, straight-chain or branched alkyl with 1 to 4 carbon atoms, halogenoalkyl with up to 3 carbon atoms and up to 5 identical or different halogen atoms (preferred halogens being fluorine and chlorine and trifluoromethyl being mentioned as an example), alkenyl or alkynyl with in either case 2 to 4 carbon atoms, cycloalkyl with 5 to 7 carbon atoms or aralkyl with 6 to 10 carbon atoms in the aryl part and 1 to 4 carbon atoms in the alkyl part (especially benzyl), it being possible for the aralkyl radical to carry one or more substituents in the aryl part selected from halogen, alkyl with 1 to 4 carbon atoms, alkoxy with 1 or 2 carbon atoms, alkylthio with 1 or 2 carbon atoms, cyano, nitro and halogenoalkyl with up to 2 carbon atoms and up to 5 identical or different halogen atoms (preferred halogens being fluorine or chlorine and trifluoromethyl being mentioned as a specific example of halogenoalkyl);

$R^5$ represents straight-chain or branched alkyl with 1 to 4 carbon atoms;

$R^6$ represents straight-chain or branched alkyl with 1 to 4 carbon atoms, fluorine, chlorine or bromine; and $R^9$ represents chlorine, bromine or iodine.

Surprisingly, the tolerance by crop plants of herbicidal active compounds of the formulae (II), (III) and (IV) and of acid addition salts or metal salt complexes of active compounds of the formula (II) is markedly improved by also using N,N-diallyl-dichloroacetamide, of the formula (I). It is also unexpected that the active compound combinations, according to the invention, of N,N-diallyldichloroacetamide of the formula (I) and at least one acetanilide of the formulae (II), (III) and (IV) have better selective herbicidal properties than the active compounds in question by themselves, in particular for selectively combating weeds in crops of useful plants.

The N,N-diallyldichloroacetamide of the formula (I) which can be used according to the invention is already known (see DE-OS (German Published Specification) No. 2,218,097). It can be prepared by reacting diallylamine with dichloroacetyl chloride, if appropriate in the presence of an acid-binding agent, such as triethylamine, dimethylbenzylamine or pyridine, and if appropriate in the presence of a diluent, for example methylene chloride or acetonitrile, at temperatures between 0° C. and 40° C. Diallylamine employed in excess can also simultaneously function as the acid-binding agent in this reaction; in this case, use of an additional acid-binding agent is superfluous.

The preparation of the N,N-diallyl-dichloroacetamide of the formula (I) which can be used according to the invention is illustrated in the example which follows:

EXAMPLE 1

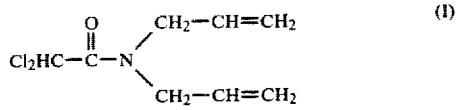

14.8 g (0.1 mol) of dichloroacetyl chloride were added to a solution of 19.4 g (0.2 mol) of di-allylamine in 200 ml of acetonitrile at room temperature, while stirring.

Thereafter, the mixture was stirred at room temperature for a further 2 hours. The reaction mixture was then poured into water. The mixture which formed was extracted several times with methylene chloride. The combined organic phases were washed successively with dilute hydrochloric acid and water, dried over magnesium sulphate and concentrated under reduced pressure. The residue which remained was subjected to fractional distillation. N,N-Diallyl-dichloroacetamide was obtained in this manner.

As already mentioned, N,N-diallyldichloroacetamide of the formula (I) which can be used according to the invention is suitable for improving the tolerance by crop plants of herbicidally active acetanilides of the formula (II), (III) and (IV) and of acid-addition salts or metal-salt complexes of active compounds of the formula (II).

Specific examples of acetanilides of the formula (II) and acid-addition salts derived therefrom are: 2-methyl-6-ethyl-N-(pyrazol-1-yl-methyl)-chloroacetanilide, 2,6-diethyl-N-(pyrazol-1-yl-methyl)-chloroacetanilide, 2,6-diethyl-N-(1,2,4-triazol-1-yl-methyl)-chloroacetanilide, 2,6-dimethyl-N-(1,2,4-triazol-1-yl-methyl)-chloroacetanilide, 2-methyl-N-(pyrazol-1-yl-methyl)-chloroacetanilide, 2,5-dimethyl-N-(pyrazol-1-yl-methyl)-chloroacetanilide, 2,3-dimethyl-N-(pyrazol-1-yl-methyl-chloroacetanilide, 2-methyl-6-ethyl-N-(pyrazol-1-yl-methyl-chloroacetanilide hydrochloride, 2,6-diethyl-N-(pyrazol-1-yl-methyl)-chloroacetanilide hydrochloride, 2,6-diethyl-N-[(3,5-dimethylpyrazol-1-yl)-methyl]-chloroacetanilide, 2,6-diethylN-[(3-chloro-1,2,4-triazolyl)-methyl]-chloroacetanilide, 2-methyl-6-ethyl-N-[(3,5-dimethyl-pyrazol-1-yl)-methyl]-chloroacetanilide, 2-tert.-butyl-N-(pyrazol-1-yl-methyl)-chloroacetanilide, 2-methyl-6-ethyl-N-[(3-bromo-5-methylpyrazol-1-yl)-methyl]-chloroacetanilide, 2-methyl-6-ethyl-N-[(4-chloro-pyrazol-1-yl)-methyl]-chloroacetanilide, 2-methyl-6-ethyl-N-[(3-chloro-1,2,4-triazolyl)-methyl]-chloroacetanilide and 2,6-diethyl-N-[(4-chloro-pyrazol-1-yl)-methyl]-chloroacetanilide.

Specific examples of acetanilides of the formula(III) are: 2,6-dimethyl-N-(benzoyl-methyl)-chloroacetanilide, 2,6-dimethyl-N-(4-chlorobenzoyl-methyl)-chloroacetanilide and 2-methyl-6-ethyl-N-(benzoyl-methyl)-chloroacetanilide.

Specific examples of acetanilides of the formula (IV) are: 2,6-diethyl-N-[(2-methyl-1,3,4-oxadiazol-5-yl)-methyl]-chloroacetanilide, 2,6-dimethyl-N-[(2-methyl-1,3,4-oxadiazol-5-yl)methyl]-chloroacetanilide, 2-ethyl-6-methyl-N-[(2-methyl-1,3,4-oxadiazol-5-yl)-methyl]-chloroacetanilide and 2-tert.-butyl-N-[(2-methyl-1,3,4-oxadiazol-5-yl)-methyl]-chloroacetanilide.

The herbicidally active acetanilides of the formula (II) and acid addition salts and metal salt complexes thereof have not hitherto been described in the literature. However, they can be prepared by (a) reacting N-halogenomethyl-halogenoacetanilides of the general formula

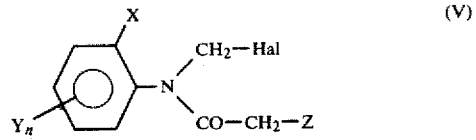

in which

X, Y, Z and n have the meanings stated above and
Hal represents halogen, especially chlorine or bromine, with heterocyclic compounds of the general formula

in which

R has the meaning stated above and
M represents hydrogen or an alkali metal, if appropriate in the presence of a diluent and of an acid-binding agent, and then optionally adding on an acid or a metal salt.

If 2,6-diethyl-N-chloromethyl-chloroacetanilide and pyrazole are used as starting substances, the course of the reaction in process (a) can be represented by the equation which follows:

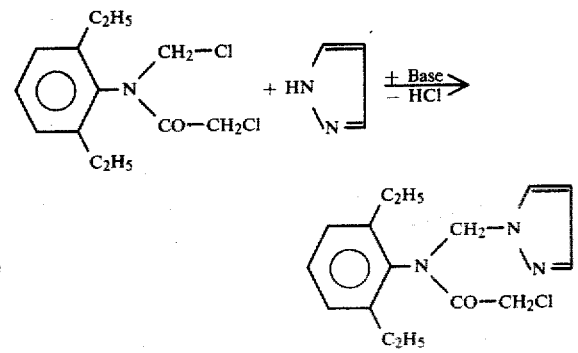

The N-halogenomethyl-halogenoacetanilides of the formula (VI), to be used as starting materials in process (a), are known, or they can be prepared by known methods (see U.S. Pat. Nos. 3,630,716 and 3,637,847). They are obtained, for example, by reacting corresponding anilines with paraformaldehyde in the presence of catalytic amounts of potassium hydroxide, and adding a halogenoacetyl halide, for example chloroacetyl chloride, to the phenylazomethines formed.

The N-halogenomethyl-halogenoacetanilides of the formula (V) can also be obtained by a new process, by reacting known halogenoacetanilides of the general formula

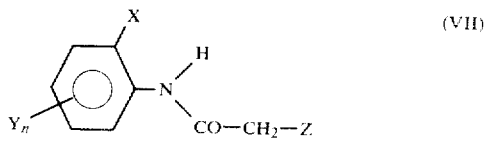

in which X, Y, Z and n have the meanings stated above, with, per mole, at least 1 mole of formaldehyde or a substance which releases formaldehyde, for example paraformaldehyde, and a halogenoating agent, such as a hydrogen halide acid or an inorganic or organic acid halide, and a water-binding agent, for example sodium sulphate, in a manner which is in itself known, at temperatures between 10° C. and 150° C., preferably between 10° and 70° C., if appropriate in the presence of an inert organic solvent, for example toluene (see German Offenlegungsschriften (German Published Specifications) Nos. 2,119,518 and 2,210,603). When inorganic acid halides, for example thionyl chloride, are employed, the use of a specific water-binding agent can be dispensed with (see also the preparative examples herein).

The formula (VI) provides a general definition of the heterocyclic compounds also to be used as starting substances. In this formula, M preferably presents hydrogen, sodium or potassium.

The heterocyclic compounds of the formula (VII) are generally known compounds of organic chemistry.

Preferred diluents for the reaction according to process (a) are inert organic solvents, especially ketones, such as diethyl ketone, and in particular methyl isobutyl ketone; nitriles, such as propionitrile, and in particular acetonitrile; ethers, such as tetrahydrofuran or dioxan; aliphatic and aromatic hydrocarbons, such as petroleum ether, benzene, toluene or xylene, or halogenated hydrocarbons, such as methylene chloride, carbon tetrachloride, chloroform or chlorobenzene; esters, such as ethyl acetate; and formamides, such as, in particular, dimethylformamide.

Acid-binding agents which can be employed in process (a) are all the inorganic and organic acid acceptors which can customarily be used, especially alkali metal carbonates, for example sodium carbonate, potassium carbonate and sodium bicarbonate, and furthermore lower tertiary alkylamines, aralkylamines, aromatic amines or cycloalkylamines, for example triethylamine, dimethylbenzylamine, pyridine and diazabicyclooctane. It is also possible to use an appropriate excess of azole, by which there is to be understood, in the present case, a compound of the formula (VI).

The reaction temperatures can be varied within a substantial range in process (a). In general, the reaction is carried out between 0° and 120° C., preferably between 20° and 80° C.

In carring out process (a), 1 to 2 moles of the heterocyclic compound of the formula (VI) and 1 mole of acid-binding agent are preferably employed per mole of the compounds of the formula (V). In order to isolate the compounds of the formula (II), the reaction mixture is filtered and the filtrate is washed with water, dried and concentrated. The residue is purified, if appropriate, by fractional crystallization or distillation.

In a particular form of working up, the reaction mixture is cooled to about 0° C. and filtered and hydrogen chloride is passed into the filtrate at 5° to -15° C. The chloride salts which have precipitated are filtered off, washed with an organic solvent, for example ethyl acetate, and partitioned in a mixture of an organic solvent, for example ethyl acetate, and water, with a pH value of about 12. The organic phase is separated off and the compounds of the formula (II) are isolated in the customary manner.

All the acids, which lead to physiologically acceptable salts, can be used for the preparation of acid-addition salts of the compounds of the formula (II). Preferred acids include the hydrogen halide acids (for example hydrobromic acid and especially hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicyclic acid, sorbic acid and lactic acid), and sulphonic acids (for example, p-toluene-sulphonic acid and 1,5-naphthalenedisulphonic acid).

The salts of the compounds of the formula (II) can be obtained in a simple manner by customary salt formation methods, for example by dissolving a compound of the formula (II) a suitable inert solvent and adding the acid, for example hydrochloric acid, and can be isolated in a known manner, for example by filtration, and if appropriate purified by washing with an inert organic solvent.

Salts of metals of main groups II to IV and of subgroups I and II and IV to VIII of the Periodic Table are preferably used for the preparation of metal salt complexes of the compounds of the formula (II), examples of metals which may be mentioned being copper, zinc, manganese, magnesium, tin, iron and nickel. Possible anions of these salts are those which are derived from acids, which lead to physicologically acceptable salts, preferably the hydrogen halide acids (for example hydrochloric acid and hydrobromic acid), phosphoric acid, nitric acid and sulphuric acid.

The metal salt complexes of the compounds of the formula (II) can be obtained in a simple manner by customary processes, thus, for example, by dissolving the metal salt in alcohol, for example ethanol, and adding the solution to the compound of the formula (II). The metal salt complexes can be isolated in a known manner, for example by filtration, and if appropriate purified by recrystallization.

The preparation of acetanilides of the formula (II) is illustrated in the examples which follow.

EXAMPLE 2

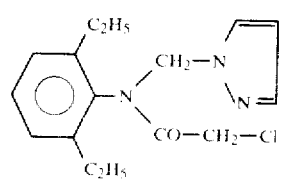

A mixture of 68 g (1 mole) of pyrazole and 106 g (1.05 moles) of triethylamine in 150 ml of anhydrous ethyl acetate were added to 274.2 g (1 mole) of 2,6-diethyl-N-chloromethyl-chloroacetanilide in 250 ml of anhydrous ethyl acetate, while stirring, during which the temperature rose to 30° C. The mixture was subsequently stirred at room temperature for 1 hour. Two possibilities for the working up were as follows:

(1) The reation mixture was filtered and the filtrate was washed with water until neutral, dried over sodium sulphate and evaporated in vacuo. After fractional crystallization of the residue with ligroin, 171.2 g (56% of theory) of 2,6-diethyl-N-(pyrazol-1-yl-methyl)-chloroacetanilide of melting point 67° C. were obtained in the form of colorless crystals.

(2) The reaction mixture was cooled to 0° C. and filtered and the residue on the filter was rinsed with 10 ml of cold ethyl acetate. 50 g (1.4 moles) of dry hydrogen chloride were passed into the filtrate at 0° to −10° C. The hydrochloride salts which had precipitated were then filtered off and rinsed with 50 ml of cold ethyl acetate and the solid residue was partitioned between 0.5 liter of ethyl acetate and 0.5 liter of aqueous sodium hydroxide solution with a pH value of 12. The organic phase was separated off, washed twice with 0.5 liter of sodium chloride solution each time, dried over sodium sulphate and evaporated in vacuo. 60 ml of benzine were added to the colorless oily residue, whereupon the residue crystallized. 220.2 g (72% of theory) of 2,6-diethyl-N-(pyrazol-1-yl-methyl)-chloroacetanilide of melting point 67° C. were obtained in the form of colorless crystals.

The compounds listed in the table which follows were prepared in an analogous manner:

TABLE 1

(II)

| Example No. | X | $Y_n$ | Z | R | Melting point (°C.) |
|---|---|---|---|---|---|
| 3 | $C_2H_5$ | 6-$C_2H_5$ | Cl | 1,2,4-Triazol-1-yl | 112 |
| 4 | i-$C_3H_7$ | 6-i-$C_3H_7$ | Cl | Pyrazol-1-yl | 134 |
| 5 | $CH_3$ | 6-$C_2H_5$ | Cl | 1,2,4-Triazol-1-yl | 92 |
| 6 | $CH_3$ | 6-$C_2H_5$ | Cl | Pyrazol-1-yl | 57 |
| 7 | $C_2H_5$ | 4,6-$(CH_3)_2$ | Cl | Pyrazol-1-yl | 82 |
| 8 | $CH_3$ | 4,6-$(CH_3)_2$ | Cl | Pyrazol-1-yl | 92 |
| 9 | $C_2H_5$ | 4-$CH_3$, 6-$C_2H_5$ | Cl | Pyrazol-1-yl | 78 |
| 10 | i-$C_3H_7$ | 6-i-$C_3H_7$ | Cl | 1,3,4-Triazol-1-yl | 196 |
| 11 | i-$C_3H_7$ | 6-i-$C_3H_7$ | Cl | 1,2,4-Triazol-1-yl | 138 |
| 12 | $C_2H_5$ | 6-$C_2H_5$ | Cl | Pyrrol-1-yl | Oil |
| 13 | i-$C_3H_7$ | -- | Cl | 1,2,4-Triazol-1-yl | 118 |
| 14 | $CH_3$ | 6-$C_2H_5$ | Cl | 1,2,3,4-Tetrazol-1-yl | Oil |
| 15 | i-$C_3H_7$ | -- | Cl | Pyrazol-1-yl | Oil |
| 16 | $C_2H_5$ | -- | Cl | 1,2,4-Triazol-1-yl | 81 |
| 17 | $CH_3$ | 6-$CH_3$ | Cl | Pyrazol-1-yl | 82 |
| 18 | $CH_3$ | 6-$CH_3$ | Cl | 1,2,4-Treazol-1-yl | 110 |
| 19 | $CH_3$ | 5-$CH_3$ | Cl | 1,2,4-Triazol-1-yl | Oil |
| 20 | $CH_3$ | -- | Cl | Pyrazol-1-yl | 56 |
| 21 | $CH_3$ | | Cl | 1,2,4-Triazol-1-yl | 88 |
| 22 | $CH_3$ | 5-$CH_3$ | Cl | Pyrazol-1-yl | Oil |
| 23 | $CH_3$ | 3-$CH_3$ | Cl | 1,2,4-Triazol-1-yl | 114 |
| 24 | $CH_3$ | 3-$CH_3$ | Cl | Pyrazol-1-yl | 102 |
| 25 | $C_2H_5$ | 6-$CH_3$ | Cl | Pyrazol-1-yl (·HCl) | 87 |
| 26 | $C_2H_5$ | 6-$C_2H_5$ | Cl | Pyrazol-1-yl | 67 |

TABLE 1-continued (II)

| Example No. | X | $Y_n$ | Z | R | Melting point (°C.) |
|---|---|---|---|---|---|
| 27 | $C_2H_5$ | 6-$C_2H_5$ | Cl | 3,5-Dimethyl-pyrazol-1-yl (·HCl) | 111 |
| 28 | $C_2H_5$ | 6-$C_2H_5$ | Cl | Bromo-methyl-pyrazolyl | 145 |
| 29 | $C_2H_5$ | 6-$C_2H_5$ | Cl | 3-Chloro-1,2,4-triazol-1-yl | 110 |
| 30 | $CH_3$ | 6-$C_2H_5$ | Cl | 3,5-Dimethyl-pyrazol-1-yl | 90 |
| 31 | $C_2H_5$ | 6-$C_2H_5$ | Cl | 3-Methyl-pyrazol-1-yl | 89 |
| 32 | $C_2H_5$ | 6-$CH_3$ | Cl | 3-Methyl-pyrazol-1-yl | 113 |
| 33 | $C(CH_3)_3$ | -- | Cl | Pyrazol-1-yl | Oil |
| 34 | $C(CH_3)_3$ | -- | Cl | 1,2,4-Triazol-1-yl | 118 |
| 35 | $C_2H_5$ | 6-$CH_3$ | Cl | Bromomethyl-pyrazolyl | 80 |
| 36 | $CH_3$ | 6-$C_2H_5$ | Cl | 4-Chloro-pyrazol-1-yl | 91 |
| 37 | $CH_3$ | 6-$C_2H_5$ | Cl | 3-Chloro-1,2,4-triazol-1-yl | 121 |
| 38 | $C_2H_5$ | 6-$CH_3$ | Cl | 2,4,5-Trichloro-imidazol-1-yl | 158 |
| 39 | $C_2H_5$ | 6-$C_2H_5$ | Cl | 4-Chloro-pyrazol-1-yl | 110 |
| 40 | $C_2H_5$ | 6-$C_2H_5$ | Cl | 1,2,3,4-Tetrazol-1-yl | 110 |
| 41 | $C_2H_5$ | 6-$C_2H_5$ | Br | Pyrazol-1-yl | 68 |
| 42 | $CH_3$ | 6-$C_2H_5$ | Br | Pyrazol-1-yl | 67 |
| 43 | $C_2H_5$ | 6-$C_2H_5$ | Cl | Imidazol-1-yl | Oil |
| 44 | $C_2H_5$ | 6-$C_2H_5$ | Br | 1,2,4-Triazol-1-yl | 90 |
| 45 | $CH_3$ | 6-$C_2H_5$ | Br | 1,2,4-Triazol-1-yl | 78 |

PREPARATION OF THE STARTING SUBSTANCES EXAMPLE 2a

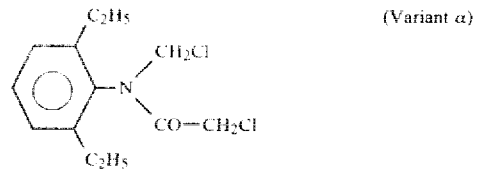

(Variant α)

45 g (1.5 moles) of paraformaldehyde were added to a solution of 225.7 g (1 mole) of 2,5-diethyl-chloroacetanilide in 1.5 liters of toluene. The mixture was warmed to 40° C. and 179 g (1.5 moles) of thionyl chloride were added dropwise, while stirring, whereupon vigorous evolution of gas started. The mixture was subsequently stirred at 40° C. until the evolution of gas had ended. Thereafter, it was filtered and the filtrate was concentrated in vacuo. After degassing the residue under a high vacuum, 268.7 g (98% of theory) of 2,6-diethyl-N-chloromethylchloroacetanilide were obtained as a colorless oil. (Variant β)

45 g (1.5 moles) of paraformaldehyde and 100 g of anhydrous sodium sulphate were added to a solution of 225.7 g (1 mole) of 2,6-diethyl-chloroacetanilide in 1.5 liters of anhydrous toluene. Dry hydrogen chloride was passed into the mixture, while stirring and warming to 50° C., until the milky suspension of the paraformaldehyde had disappeared. Thereafter, a further 100 g of anhydrous sodium sulphate were added and the mixture was subsequently stirred at 50° C. for one hour and filtered. The filtrate was concentrated in vacuo. After degassing the residue, 263.2 g (96% of theory) of 2,6-diethyl-chloroacetanilide were obtained as a colorless oil.

The compounds in Table 2 which follows were obtained analogously to Example 2a.

TABLE 2

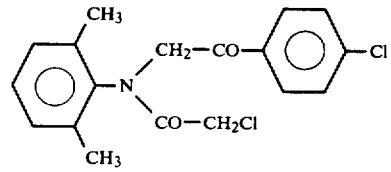

| Example No. | X | $Y_n$ | Z | Hal | Melting point or refractive index |
|---|---|---|---|---|---|
| 4 a | i-C₃H₇ | 6-i-C₃H₇ | Cl | Cl | not isolated |
| 5 a | CH₃ | 6-C₂H₅ | Cl | Cl | 91 |
| 7 a | C₂H₅ | 4,6-(CH₃)₂ | Cl | Cl | not isolated |
| 8 a | CH₃ | 4,6-(CH₃)₂ | Cl | Cl | " |
| 9 a | C₂H₅ | 4-CH₃ 6-C₂H₅ | Cl | Cl | " |
| 13 a | i-C₃H₇ | — | Cl | Cl | 90 |
| 16 a | C₂H₅ | — | Cl | Cl | not isolated |
| 17 a | CH₃ | 6-CH₃ | Cl | Cl | 88 |
| 19 a | CH₃ | 5-CH₃ | Cl | Cl | not isolated |
| 23 a | CH₃ | 3-CH₃ | Cl | Cl | 40 |
| 33 a | C(CH₃)₃ | — | Cl | Cl | not isolated |
| 41 a | C₂H₅ | 6-C₂H₅ | Br | Br | " |
| 42 a | CH₃ | 6-C₂H₅ | Br | Br | " |

The acetanilides of the formula (II) display powerful herbicidal actions, in particular against grasses. They can therefore be employed for selectively combating weeds, in particular graminaceous weeds.

The herbicidally active acetanilides of the formula (III) likewise have not hitherto been described in the literature. However, they can be prepared by reacting (b) N-acylmethylanilines of the general formula

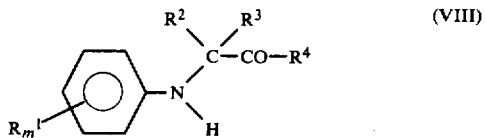

in which $R^1$, $R^2$, $R^3$, $R^4$ and m have the meanings stated above, with chloroacetyl chloride in the presence of a diluent.

If 2,6-dimethyl-N-benzoylmethyl-aniline and chloroacetyl chloride are used as starting substances, the course of the reaction in process (b) can be represented by the equation which follows:

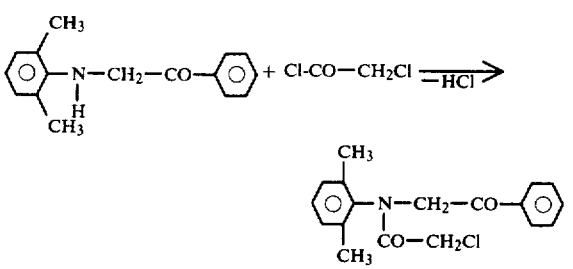

The N-acylmethyl-anilines of the formula (VIII) are known (see, inter alia, Chem. Ber. 25, 2865 (1892) and Chem. Soc. 1943, 63), or they can be prepared by known methods. They are obtained, for example, by reacting anilines with α-halogenoketones in the presence of an organic solvent, for example ethanol (see also the preparative examples herein).

Preferred diluents for the reaction according to process (b) are inert organic solvents, especially ketones, such as diethyl ketone, and in particular acetone and methyl ethyl ketone; nitriles, such as propionitrile, and in particular acetonitrile; ethers, such as tetrahydrofuran or dioxan; aliphatic and aromatic hydrocarbons, such as petroleum ether, benzene, toluene or xylene; halogenated hydrocarbons, such as methylene chloride, carbon tetrachloride, chloroform or chlorobenzene; and esters, such as ethyl acetate.

The reaction temperatures can be varied within a substantial range in carrying out process (b). In general, the process is carried out between 0° and 120° C., preferably between 20° and 100° C.

In carrying out process (b), 1 to 3 moles of chloroacetyl chloride are preferably employed per mole of the compound of the formula (IX). Isolation of the compounds of the formula (III) is effected in the customary manner.

The preparation of acetanilides of the formula (III) is illustrated in the examples which follow:

EXAMPLE 46

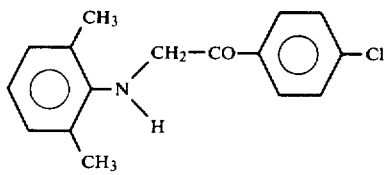

16 ml (0.2 mole) of chloroacetyl chloride were added dropwise to a solution of 18.5 g (0.068 mole) of 2,6-dimethyl-N-(4-chloro-benzoylmethyl)-aniline in 150 ml of benzene. Thereafter, the mixture was stirred under reflux for 15 hours and concentrated by distilling off the solvent and excess chloroacetyl chloride in vacuo. The residue was triturated with an ether/petroleum ether mixture (1:3) and the crystalline residue which formed was filtered off and dried. 17.7 g (75% of theory) of 2,6-dimethyl-N-(4-chlorobenzoylmethyl)-chloroacetanilide of melting point 128° C. were obtained.

PREPARATION OF THE STARTING MATERIAL 46.7 g (0.2 mole) of ω-bromo-4-chloroacetophenone in 40 ml of ethanol were added to 48.4 g (0.4 mole) of 2,6-dimethylaniline in 40 ml of ethanol and the mixture was warmed to 50° C. for 20 minutes. Thereafter, it was cooled to 0° C. and the crystals which had formed were filtered off and rinsed with a little ethanol. 30 g (55% of theory) of 2,6-dimethyl-N-(4-chlorobenzoylmethyl)-aniline of melting point 82° C. were obtained.

EXAMPLE 47

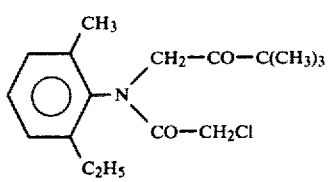

23.3 g (0.1 mole) of 2-ethyl-6-methyl-N-pivaloyl-methyl-aniline were dissolved in 100 ml of benzene, and 24 ml (0.3 mole) of chloroacetyl chloride were added. Thereafter, the mixture was stirred under reflux for 15 hours and concentrated by distilling off the solvent and excess chloroacetyl chloride in vacuo. The oily residue was stirred with petroleum ether, the product phase was decanted, stirred with active charcoal and filtered and the filtrate was concentrated in vacuo. The residue was stirred with n-hexane and the resulting solid was filtered off and dried. 13.7 g (45% of theory) of 2-ethyl-6-methyl-N-pivaloylmethyl-chloroacetanilide of melting point 86° C. were obtained.

PREPARATION OF THE STARTING MATERIAL

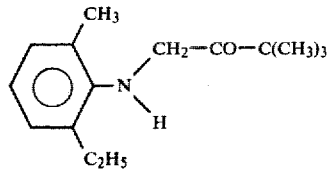

108 g (0.8 mole) of 2-ethyl-6-methyl-aniline and 53.8 g (0.4 mole) of monochloropinacolin were heated to 110° C. in 300 ml of toluene for 25 hours. The mixture was allowed to cool and was filtered and the filtrate was washed with water, dried over sodium sulphate and concentrated by distilling off the solvent in vacuo. The residue was subjected to fractional distillation. 24.1 g (26% of theory) of 2-ethyl-6-methyl-N-pivaloylmethylaniline of boiling point 138 to 150° C./0.7 mm Hg and with a refractive index of $n_D^{20} = 1.5168$ were obtained.

The compounds listed in Table 3 which follows were prepared in a manner analogous to Example 46 or 47.

TABLE 3

(III)

| Example No. | $R_m^1$ | $R^2$ | $R^3$ | $R^4$ | Melting point (°C.) or refractive index |
|---|---|---|---|---|---|
| 48 | 2-CH$_3$ | H | H | ⌬ | 138 |
| 49 | 2-CH$_3$ | H | H | ⌬—Cl | 140 |
| 50 | 2,6-(C$_2$H$_5$)$_2$ | H | H | ⌬—Cl | 134 |
| 51 | 2,6-(C$_2$H$_5$)$_2$ | H | H | ⌬ | 116 |
| 52 | 2-Cl | H | H | ⌬—Cl | 124 |
| 53 | 2,6-(CH$_3$)$_2$ | H | H | ⌬ | 100 |
| 54 | 4-Cl | H | H | ⌬—Cl | 114 |
| 55 | 2,6-(CH$_3$)$_2$ | CH$_3$ | H | CH$_3$ | 104 |
| 56 | 2,6-(i-C$_3$H$_7$)$_2$ | H | H | ⌬—Cl | 200 |
| 57 | 2,6-(C$_2$H$_5$)$_2$, 4-CH$_3$ | H | H | ⌬ | 112 |
| 58 | 2,6-(i-C$_3$H$_7$)$_2$ | H | H | ⌬ | 140 |
| 59 | 2,6-(CH$_3$)$_2$ | H | H | ⌬(CH$_3$)(CH$_3$) | 90 |

TABLE 3-continued

Structure (III):

$R_m^1$-phenyl-N(CO-CH$_2$Cl)-C(R$^2$)(R$^3$)-CO-R$^4$

| Example No. | $R_m^1$ | $R^2$ | $R^3$ | $R^4$ | Melting point (°C.) or refractive index |
|---|---|---|---|---|---|
| 60 | 2-C$_2$H$_5$, 6-CH$_3$ | H | H | 4-Cl-phenyl | 70 |
| 61 | 2,6-(CH$_3$)$_2$ | H | H | 3,4-(OCH$_3$)$_2$-phenyl | 114 |
| 62 | 2-C$_2$H$_5$, 4,6-(CH$_3$)$_2$ | H | H | phenyl | $n_D^{20}$ = 1.5680 |
| 63 | 2,6-(CH$_3$)$_2$ | H | H | 4-F-phenyl | 104 |
| 64 | 2,4,6-(CH$_3$)$_3$ | H | H | 4-Cl-phenyl | 134 |
| 65 | 2,4,6-(CH$_3$)$_3$ | H | H | phenyl | $n_D^{20}$ = 1.5610 |
| 66 | 2,6-(CH$_3$)$_2$ | H | phenyl | 4-Cl-phenyl | 149 |
| 67 | 2,6-(CH$_3$)$_2$ | H | CH$_3$ | phenyl | 84 |

The compounds listed in Table 4 which follows could be obtained in an analogous manner.

TABLE 4

Structure (III):

$R_m^1$-phenyl-N(CO-CH$_2$Cl)-C(R$^2$)(R$^3$)-CO-R$^4$

| Example No. | $R_m^1$ | $R^2$ | $R^3$ | $R^4$ |
|---|---|---|---|---|
| 68 | 3,5-(CF$_3$)$_2$ | H | H | 4-Cl-phenyl |
| 69 | 2,6-(CH$_3$)$_2$ | H | H | 4-NO$_2$-phenyl |
| 70 | 2,6-(CH$_3$)$_2$ | H | H | 4-CN-phenyl |
| 71 | 2,6-(CH$_3$)$_2$ | H | H | 4-C(CH$_3$)$_3$-phenyl |
| 72 | 2,6-(CH$_3$)$_2$, 4-SO$_2$NH$_2$ | H | H | 4-Cl-phenyl |
| 73 | 2-Cl, 6-CH$_3$ | H | H | 4-Cl-phenyl |
| 74 | 2-C$_2$H$_5$, 6-CH$_3$ | CH$_3$ | CH$_3$ | CH$_3$ |
| 75 | 2-C$_2$H$_5$, 6-CH$_3$ | CH$_3$ | CH$_3$ | 4-phenyl-phenyl |
| 76 | 2-C$_2$H$_5$, 6-CH$_3$ | CH$_3$ | CH$_3$ | 4-phenoxy-phenyl |
| 77 | 2-C$_2$H$_5$, 6-CH$_3$ | CH$_3$ | CH$_3$ | 4'-Cl-biphenyl |
| 78 | 2-C$_2$H$_5$, 6-CH$_3$ | CH$_3$ | CH$_3$ | 4-Cl-phenyl |
| 79 | 2-C$_2$H$_5$, 6-CH$_3$ | H | CH$_3$ | 4-Cl-phenyl |
| 80 | 2-C$_2$H$_5$, 6-CH$_3$ | H | CH$_3$ | 4'-Cl-biphenyl |
| 81 | 2,6-(CH$_3$)$_2$ | H | 4-Cl-phenyl | 4-Cl-phenyl |
| 82 | 2,6-(CH$_3$)$_2$ | H | 4-F-phenyl | 4-Cl-phenyl |
| 83 | 2,6-(CH$_3$)$_2$ | H | 3-CH$_3$-phenyl | phenyl |
| 84 | 2,6-(CH$_3$)$_2$ | H | phenyl | phenyl |

TABLE 4-continued

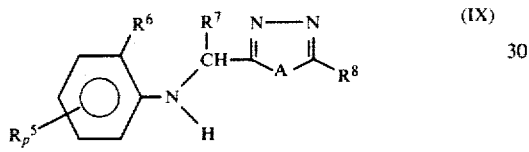

| Example No. | $R_m^1$ | $R^2$ | $R^3$ | $R^4$ |
|---|---|---|---|---|
| 85 | 2,6-(CH$_3$)$_2$ | H |  | |
| 86 | 2,6-(CH$_3$)$_2$ | H | CH$_3$ |  |

The acetanilides of the formula (III) have powerful herbicidal properties. They are therefore suitable for combating weeds. In particular, they can be employed for selective combating of broad-leaved weeds and graminaceous weeds.

The herbicidally active acetanilides of the formula (IV) likewise have not hitherto been described in the literature. However, they can be prepared by (c) reacting N-azolylalkylanilines of the general formula

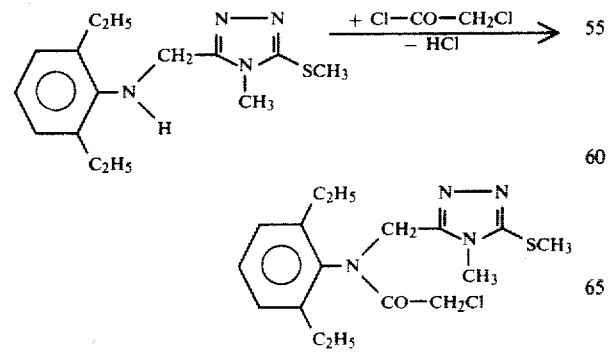

in which $R^5$, $R^6$, $R^7$, $R^8$, A and p have the meanings stated above, with halogenoacetic acid chlorides or anhydrides of the formula $$R^9-CH_2-CO-Cl \quad (Xa)$$

or $$(R^9-CH_2-CO)_2O \quad (Xb)$$

in which $R^9$ has the meaning stated above, in the presence of a diluent and if appropriate in the presence of an acid-binding agent.

If 2,6-diethyl-N-(3-methylthio-4-methyl-1,2,4-triazol-5-yl-methyl)-aniline and chloroacetyl chloride are used as starting substances, the course of the reaction of process (c) can be represented by the equation which follows:

The N-azolylalkylanilines of the formula (IX) required as starting substances in process (c) have not yet been described in the literature. They are obtained when (d) anilines of the general formula

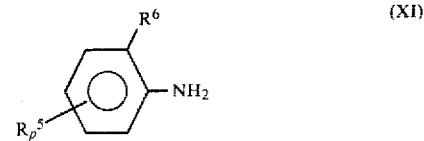

in which $R^5$, $R^6$ and p have the meanings stated above, are reacted with azole derivatives of the general formula

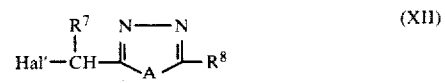

in which

A, $R^7$ and $R^8$ have the meanings stated above and
Hal' represents chlorine or bromine, in the presence of an acid-binding agent, for example potassium carbonate or sodium carbonate, and in the presence of an inert organic solvent, for example dimethylformamide or toluene, at temperatures between 20° and 160° C., an excess of the aniline of the formula (XII) preferably being employed (see also the preparative examples herein), or (e) hydrazine derivatives of the general formula

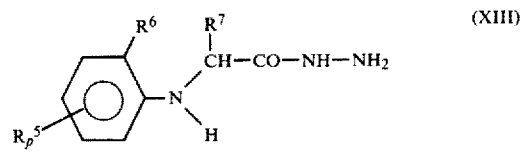

in which $R^5$, $R^6$, $R^7$ and p have the meanings stated above, are reacted with isocyanates or isothiocyanates of the general formula $$R^{10}-N=C=B \quad (XIV)$$

in which

B represents oxygen or sulphur and
$R^{10}$ has the meaning stated above, in the presence of an organic solvent, for example an alcohol, ether or hydrocarbon, at temperatures between 0° and 80° C., the compounds formed, of the general formula

in which B, $R^5$, $R^6$, $R^7$, $R^{10}$ and p have the meanings stated above, are cyclized in the presence of a strong base, for example sodium hydroxide solution or potassium hydroxide solution, and in the presence of a solvent, for example ethanol or water, at temperatures between 20° and 100° C., and the triazolones or triazolethiones formed, of the general formula

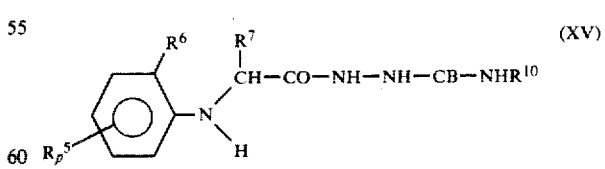

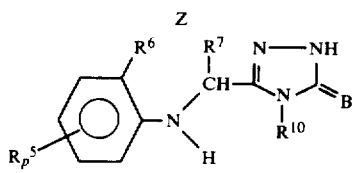
(XVI)

in which B, $R^5$, $R^6$, $R^7$, $R^{10}$ and p have the meanings stated above, are reacted with halides of the general formula $$Hal'-R^{12} \quad \text{(XVII)}$$

in which

Hal' represents chlorine or bromine and $R^{12}$ represents one of the radicals of the substituent $R^{11}$, with the exception of hydrogen, in the presence of a strong base, for example sodium hydroxide solution, and in the presence of an inert organic solvent, for example tolune or methylene chloride, at temperatures between 20° and 80° C., it also being possible to carry out the reaction under phase-transfer catalysis and with other alkylating reagents, for example dimethyl sulphate (see also the preparative examples), or (f) hydrazine derivatives of the formula (XIV) are reacted with formic acid or acid chlorides or acid anhydrides of the general formula $$R^{13}-CO-Cl \quad \text{(XVIIIa)}$$

or $$(R^{13}-CO-)_2O \quad \text{(XVIIIb)}$$

in which $R^{13}$ represents alkyl, halogenoalkyl, alkenyl, alkynyl, cycloalkyl, optionally substituted aryl or optionally substituted aralkyl, in the presence of an inert organic solvent, such as an ether, hydrocarbon or halogenated hydrocarbon, at temperatures between 0° and 50° C., and the compounds formed, of the general formula

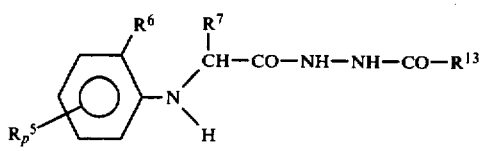
(XIV)

in which $R^5$, $R^6$, $R^7$, $R^{13}$ and p have the meanings stated above, are either cyclized with diphosphorus pentasulphide in a manner which is in itself known (see Chem. Ber. 32, 797 (1899) and J. prakt. Chemie 69, 145 (1904)) to give thiadiazole derivatives, or are reacted, also in a known manner, with customary reagents which split off water, to give oxadiazole derivatives (in this context, see Elderfield, Heterocyclic Compounds, volume 7 (1961)), or (g) hydrazine derivatives of the general formula (XIV) are reacted with nitriles of the general formula $$R^{14}-C\equiv N \quad \text{(XXI)}$$

in which $R^{14}$ represents alkyl, halogenoalkyl or, optionally substituted aryl, in a manner which is in itself known to give triazole derivatives (see Chem. Ber. 96, 1064 (1963)), or (h) hydrazine derivatives of the formula (XIV) are reacted with imino-ethers of the general formula

(XXIa)

in which $R^{13}$ represents alkyl, halogenoalkyl, alkenyl, alkynyl, cycloalkyl, optionally substituted aryl or optionally substituted aralkyl and $R^{15}$ represents methyl or ethyl, in a manner which is in itself known, under reflux and in the presence of an inert organic solvent, for example ethanol, to give oxadiazole derivatives, or (j) anilines of the general formula (XII) are reacted with azole-aldehydes of the general formula

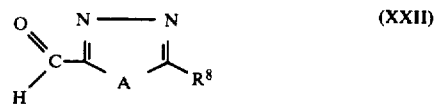
(XXII)

in which $R^8$ has the meaning stated above, in the presence of an inert organic solvent, for example toluene, at temperatures between 80° and 120° C., and the compounds formed, of the general formula

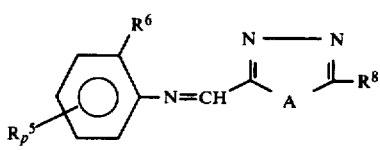
(XXIII)

in which A, $R^5$, $R^6$, $R^8$ and p have the meanings stated above, are reduced in a generally known manner; for example by reaction with complex hydrides, such as sodium borohydride, if appropriate in the presence of a polar organic solvent, such as methanol, at temperatures between 0° and 80° C.

The compounds of the formulae (XII) and (XIII) required as starting substances in process (d) are known, or they can be prepared by processes which are known in principle (see Helv. Chim. Acta 55, 199 et seq. (1972), Chem. Ber. 32, 797 et seq. (1899) and Chem. Ber. 96, 1049 et seq. (1963)).

The starting substances of the formula (XIV) required in process (e) have not yet been described in the literature. However, they can be prepared by known processes, by reacting known esters (see, inter alia, DT-OS (German Published Specification) No. 2,350,944 and 2,513,730) of the general formula

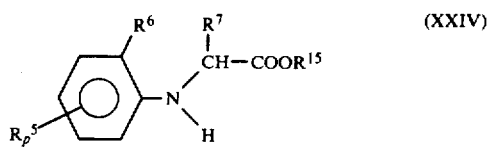
(XXIV)

in which $R^5$, $R^6$, $R^7$ and p have the meanings stated above and $R^{15}$ represents methyl or ethyl, with hydrazine hydrate, preferably in the presence of an organic solvent, for example ethanol, dioxan or dimethylformamide, at temperatures between 20° and 120° C. (see also the preparative examples herein).

The reactants of the formulae (XIV) and (XVII) required in process (e) are generally known compounds of organic chemistry.

The compounds of the formulae (XVIIIa), (XVIIIb), (XX) and (XXI) required as reactants in processes (f), (g) and (h) are likewise known.

The azole-aldehydes of the formula (XXII) to be used as reactants in process (j) are likewise known, or they can be prepared by processes which are known in principle (see Elderfield, "Heterocyclic Compounds" volume 7 (1961) and "Advances in Heterocyclic Chemistry", volume 9 (1968)).

The halogenoacetic acid chlorides and anhydrides of the formulae (Xa) and (Xb) also required as starting materials in process (c) are generally known compounds of organic chemistry.

Preferred diluents for reaction (c) are inert organic solvents, especially ketones, such as diethyl ketone, and in particular acetone and methyl ethyl ketone; nitriles, such as propionitrile, and in particular acetonitrile; ethers, such as tetrahydrofuran or dioxan; aliphatic and aromatic hydrocarbons, such as petroleum ether, benzene, toluene or xylene; halogenated hydrocarbons, such as methylene chloride, carbon tetrachloride, chloroform or chlorobenzene; and esters, such as ethyl acetate.

If appropriate, process (c) can be carried out in the presence of acid-binding agents (hydrogen chloride acceptors). All the customary acid-binding agents can be used as these agents, especially organic bases, such as tertiary amines, for example triethylamine, or such as pyridine; and inorganic bases, for example alkali metal hydroxides and alkali metal carbonates.

The reaction temperatures can be varied within a substantial range in carrying out process (c). In general, the process is carried out between 0° and 120° C., preferably between 20° and 100° C.

In carrying out process (c), 1 to 1.5 moles of halogenoacetylating agent and 1 to 1.5 moles of acid-binding agent are preferably employed per mole of the compound of the formula (X). Isolation of the compounds of the formula (IV) is effected in the customary manner.

The preparation of acetanilides of the formula (IV) is illustrated in the examples which follow.

EXAMPLE 87

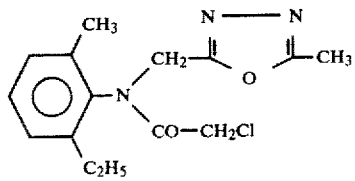

16.3 g (0.07 mole) of 2-ethyl-6-methyl-N-[(2-methyl-1,3,4-oxadiazol-6-yl)-methyl]-aniline and 6 g (0.076 mole) of anhydrous pyridine were heated to the boil in 100 ml of absolute tetrahydrofuran, while stirring, and a solution of 8 g (0.07 mole) of chloroacetyl chloride in 20 ml of tetrahydrofuran was added dropwise. When the dropwise addition had ended, the mixture was subsequently stirred for 10 minutes and concentrated by distilling off the solvent and the residue was stirred with 150 ml. of water. The reaction product which crystallized out was filtered off, washed with water and dried. 18.7 g (87% of theory) of beige-colored crystals of 2-ethyl-6-methyl-N-[(2-methyl-1,3,4-oxadiazol-5-yl)-methyl]-chloroacetanilide of melting point 67° to 70° C. were obtained.

PREPARATION OF THE STARTING MATERIAL

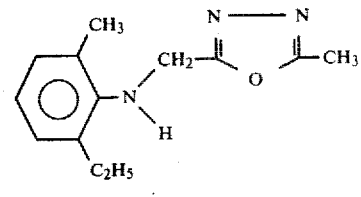

A mixture of 101.2 g (0.76 mole) of 2-ethyl-6-methyl-aniline, 40 g (0.3 mole) of 2-methyl-5-chloromethyl-1,3,4-oxadiazole, 41.4 g (0.3 mole) of powdered potassium carbonate and 76 ml of dimethylformamide was heated to 100° C. for 5 hours, while stirring. Thereafter, the reaction mixture was filtered and the filtrate was diluted with methylene chloride and washed several times with water. The methylene chloride phase was dried over sodium sulphate and concentrated in vacuo by distilling off the solvent. The residue was distilled in vacuo. 46.8 g (67.5% of theory) of a yellowish oil consisting of 2-ethyl-6-methyl-N-[(2-methyl-1,3,4-oxadiazol-5-yl)-methyl]-aniline of boiling point 140° to 142° C./0.1 mm Hg and with a purity of 94% (determined by gas chromatography) were obtained.

EXAMPLE 88

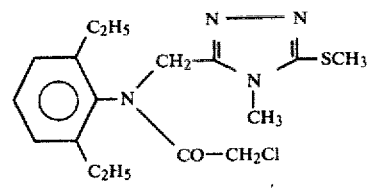

5 g (0.017 mole) of 2,6-diethyl-N-[(1-methyl-2-methylthio-1,3,4-triazol-5-yl)-methyl]-aniline and 1.6 g (0.02 mole) of pyridine were stirred in 100 ml of absolute tetrahydrofuran, and 2.3 g (0.02 mole) of chloroacetyl choride were added dropwise at room temperature, during which the temperature rose to about 30° C. The mixture was stirred for 2 hours and partly concentrated by distilling off the solvent, and water was added. The product which crystallised out was filtered off, dried and recrystallized from diisopropyl ether/ethyl acetate. 5 g (80% of theory) of 2,6-diethyl-N-[(1-methyl-2-methylthio-1,3,4-triazol-5-yl)-methyl]-chloroacetanilide of melting point 121° to 123° C. were obtained.

PREPARATION OF THE PRECURSORS

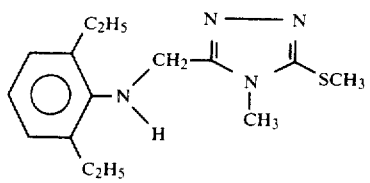
(a)

13.9 g (0.05 mole) of 2,6-diethyl-N-[(1-methyl-2-thiono-1,3,4-triazol-5-yl)-methyl]-aniline were stirred rapidly in a two-phase mixture of 150 ml of toluene and 40 ml of 50% strength sodium hydroxide solution at room temperature, 1.5 g of triethyl-benzylammonium chloride (TEBA) being added as a catalyst, and 6.3 g (0.05 mole) of dimethyl sulphate were added dropwise, during which the temperature rose to about 35° C. The mixture was stirred for 5 hours and the toluene phase was separated off, washed several times with water, dried over sodium sulphate and concentrated by distilling off the solvent. The oil which remained was made to crystallize by adding petroleum ether. After recrystallization from petroleum ether, 6.7 g (40% of theory) of 2,6-diethyl-N-[(1-methyl-2-methylthio-1,3,4-triazol-5-yl)-methyl]-aniline of melting point 65° to 67° C. were obtained.

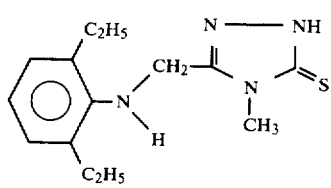
(b)

29.6 g (0.1 mole) of 1-methyl-4-[(2,6-diethylanilino)-acetyl]-thiosemicarbazide were suspended in 150 ml of ethanol and, after added 7 g of potassium hydroxide in 20 ml of water, the mixture was heated under reflux for 1 hour. Thereafter, most of the solvent was distilled off and 250 ml of water were added to the residue. After acidifying the mixture to pH 5 with glacial acetic acid, the precipitate which formed was filtered off and washed thoroughly with water. After drying, 27 g (97% of theory) of 2,6-diethyl-N-[(1-methyl-2-thiono-1,3,4-triazol-5-yl)-methyl]-aniline of melting point 117° to 121° C. were obtained.

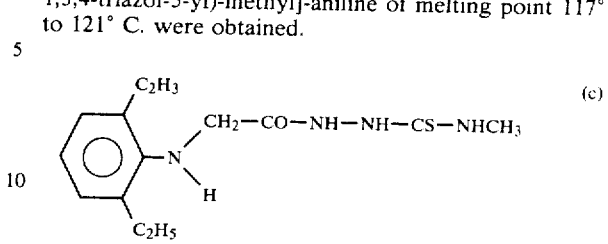
(c)

44.2 g (0.2 mole) of 2,6-diethyl-anilino-acetic acid hydrazide and 14.8 g (0.2 mole) of methyl isothiocyanate were dissolved in 250 ml of ethanol and the solution was heated to the reflux temperature for one hour. After subsequently cooling the mixture to room temperature, the precipitate which had formed was filtered off and rinsed twice with 50 ml of ethanol each time. After drying, 46 g (78% of theory) of 1-methyl-4-[(2,6-diethylanilino)-acetyl]-thiosemicarbazide were obtained in the form of a colorless crystalline substance of melting point 166° C.

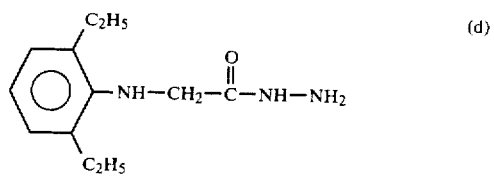
(d)

58.7 g (0.25 mole) of 2,6-diethyl-anilino-acetic acid ethyl ester and 25 g of hydrazine hydrate were left to stand in 200 ml of ethanol for 24 hours. Thereafter, the mixture was concentrated by distilling off the solvent and the residue was extracted by stirring with water. After drying, 50.5 g (91% of theory) of colorless crystals of 2,6-diethyl-anilino-acetic acid hydrazide of melting point 71° to 73° C. were obtained.

The compounds listed below in Table 5 were obtained in a manner corresponding to Example 87 or 88.

TABLE 5

(IV)

| Example No. | $R^7$ | $R^8$ | $R^6$ | $R_p^5$ | A | $R^9$ | Melting point (°C.) |
|---|---|---|---|---|---|---|---|
| 89 | H | CH$_3$ | C$_2$H$_5$ | 6-C$_2$H$_5$ | O | Cl | 79-82 |
| 90 | H | CH$_3$ | CH$_3$ | 6-CH$_3$ | O | Cl | 91-93 |
| 91 | H | CH$_3$ | C(CH$_3$)$_3$ | — | O | Cl | 102-04 |
| 92 | H | —S—CH$_2$—CH=CH$_2$ | C$_2$H$_5$ | 6-C$_2$H$_5$ | >N—CH$_3$ | Cl | 67-70 |
| 93 | H | —S—CH$_2$—C$_6$H$_4$F | CH$_3$ | 6-C$_3$H$_5$ | >N—CH$_3$ | Cl | 115-20 |
| 94 | H | C$_2$H$_5$ | CH$_3$ | 6-C$_2$H$_5$ | O | Cl | 57-59 |
| 95 | H | C$_2$H$_5$ | C$_2$H$_5$ | 6-C$_2$H$_5$ | O | Cl | 43-47 |
| 96 | H | i-C$_3$H$_7$ | CH$_3$ | 6-C$_2$H$_5$ | O | Cl | viscous oil |

TABLE 5-continued $$\text{(IV)}$$

Structure: phenyl ring with $R^6$, $R_p^5$ substituents, N bearing CH($R^7$)—[ring with N—N, A, $R^8$] and CO—CH$_2$—$R^9$

| Example No. | $R^7$ | $R^8$ | $R^6$ | $R_p^5$ | A | $R^9$ | Melting point (°C.) |
|---|---|---|---|---|---|---|---|
| 97 | H | CH$_3$ | CH$_3$ | 3-CH$_3$ | >N—(2,3-dimethylphenyl) with CH$_3$ groups | Cl | glass-like solid |
| 98 | H | CH$_3$ | C$_2$H$_5$ | 6-C$_2$H$_5$ | O | Br | 80 |
| 99 | H | CH$_3$ | CH$_3$ | 6-C$_2$H$_5$ | O | Br | 92–94 |
| 100 | H | CH$_3$ | i-C$_3$H$_7$ | 6-i-C$_3$H$_7$ | O | Cl | 135–37 |

The starting materials listed in the table which follows were obtained by one of more of the processes described in the present specification.

TABLE 6

Structure: phenyl ring with $R^6$, $R_p^5$, N—H, CH($R^7$)—[ring with N—N, A, $R^8$]

| Example No. | $R^7$ | $R^8$ | $R^6$ | $R_p^5$ | A | Melting point (°C.) or refractive index |
|---|---|---|---|---|---|---|
| IX-1 | H | CH$_3$ | C$_2$H$_5$ | 6-C$_2$H$_5$ | O | $n_D^{22} = 1.540$ |
| IX-2 | H | CH$_3$ | CH$_3$ | 6-C$_2$H$_5$ | O | $n_D^{22} = 1.547$ |
| IX-3 | H | CH$_3$ | CH$_3$ | 6-CH$_3$ | O | $n_D^{22} = 1.552$ |
| IX-4 | H | CH$_3$ | —(CH$_3$)$_3$ | — | O | 52–55 |
| IX-5 | H | CH$_3$ | i-C$_3$H$_7$ | 6-i-C$_3$H$_7$ | O | 96–99 |
| IX-6 | H | C$_2$H$_5$ | C$_2$H$_5$ | 6-C$_2$H$_5$ | O | $n_D^{22} = 1.534$ |
| IX-7 | H | C$_2$H$_5$ | CH$_3$ | 6-C$_2$H$_5$ | O | $n_D^{21} = 1.542$ |
| IX-8 | H | i-C$_3$H$_7$ | CH$_3$ | 6-C$_2$H$_5$ | O | $n_D^{21} = 1.531$ |
| IX-9 | H | SCH$_3$ | C$_2$H$_5$ | 6-C$_2$H$_5$ | >N—CH$_3$ | 65–57 |
| IX-10 | H | S—CH$_2$—CH=CH$_2$ | C$_2$H$_5$ | 6-C$_2$H$_5$ | >N—CH$_3$ | $n_D^{21} = 1.577$ |
| IX-11 | H | S—CH$_2$—(2-F-phenyl) | CH$_3$ | 6-C$_2$H$_5$ | >N—CH$_3$ | viscous oil |
| IX-12 | H | CH$_3$ | CH$_3$ | 3-CH$_3$ | >N—(2,3-dimethylphenyl) | 142–143 |

The acetanilides of the formula (IV) have powerful herbicidal properties, in particular selective herbicidal properties. They are therefore suitable for combating weeds. In particular, they can be employed for selectively combating broad-leaved weeds and graminaceous weeds. Their selectivity is not always satisfactory.

The antidote which can be used according to the invention, that is to say N,N-diallyl-dichloroacetamide of the formula (I), is particularly suitable for improving the tolerance of herbicidally active acetanilides of the formulae (II), (III) and (IV) and of acid addition salts or metal salt complexes of active compounds of the formula (II) by important crop plants, such as corn, soya beans, cotton, sugar beet, cereals, rice and cane sugar.

The active compound combinations according to the invention exhibit a very good action against broad-leaved weeds and graminaceous weeds in numerous crops of useful plants. They can therefore be used for selectively combating weeds in numerous crops of useful plants. By weeds, in the broadest sense, there are to be understood in this context all plants which grow in locations where they are undesired.

The active compound combinations according to the invention can be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea, and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostic, Alopecurus and Apera.

The active-compound combinations according to this invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita, and monocotyledon cultures of the genera Oryza, Zea, Triticum, Hordeum, Avena, Secale, Sorghum, Panicum, Saccharum, Ananas, Asparagus and Allium.

The active-compound combinations according to the invention are particularly suitable for selectively combating weeds in corn, soya beans, cotton, sugarbeet, cereals, rice and cane sugar.

The antidote which can be used according to the invention can be converted, if appropriate as a mixture with the herbicidal active compounds with which it is employed, into the customary formulations, such as solutions, emulsions, wettable powders, suspensions, powders, dusting agents, foams, pastes, soluble powders, granules, suspension-emulsion concentrates, natural and synthetic materials impregnated with active compound, and very fine capsules in polymeric substances.

These formulations are produced in known manner, for example by mixing the antidote which can be used according to the invention, of appropriate as a mixture with the herbicidal active compounds with which it is employed, with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95% by weight of antidote or antidote and herbicidal active compound, preferably from 0.5 to 90%.

The antidote which can be used according to the invention, as such or in the form of its formulations, can also be employed as mixtures with herbicidal active compounds, finished formulations or tank mixing being possible. Mixtures with other known active compounds, such as fungicides, insecticides, acaricides, nematicides, bird repellants, growth factors, plant nutrients and agents which improve soil structure are also possible.

The antidote which can be used according to the invention or mixtures of the antidote which can be used according to the invention and a herbicidal active compound can be employed as such, in the form of their formulations or in the use forms prepared therefrom by further dilution, such as ready-to-use solutions, suspensions, emulsions, powders and granules. They may be used in the customary manner, for example by watering, spraying, atomizing, dusting, scattering, dry dressing, moist dressing, wet dressing, slurry dressing or encrusting.

The antidote which can be used according to the invention can be applied by methods customary for antidotes of this type. Thus, the antidote which can be used according to the invention can be applied either before or after the herbicide, or can be applied together with the herbicide. If the herbicide is used before or after sowing, crop plants can also be protected against damage by treating the seed with the antidote before sowing (dressing). A further possible way of using the antidote is to apply it to the seed furrow during sowing. If the plants are seedlings, these can be treated with the antidote before being transplanted.

When the antidote which can be used according to the invention is employed, the amounts customarily used, at the location, of the particular herbicides are applied. The amounts of herbicidal active compound in general will vary between 0.1 and 5 kg/ha. The amount of antidote used is independent of the herbicide and of the amount of herbicidal active compound used. In general, the applied amounts of antidote which can be used according to the invention are between 0.1 and 5 kg/ha in the case of treatment of the soil surface, preferably between 0.2 and 4 kg/ha. In the case of seed treatment, the applied amounts of antidote which can be used according to the invention are in general between 10 and 300 g per kilogram of seed, preferably between 25 and 200 g per kilogram of seed.

The weight ratios of antidote to herbicidal active compound in the active compound combinations according to the invention can vary within relatively wide limits. In general, 0.05 to 1.0 part by weight, preferably 0.1 to 0.5 part by weight, of antidote of the formula (I) is present per part by weight of herbicidal active compound of the formula (II), (III) or (IV).

The good activity of the antidote which can be used according to the invention and of the active compound combinations according to the invention can be seen from the example which follows.

EXAMPLE A

Pre-emergence test

Solvent: 5 parts by weight of acetone
Emulsifier: 1 part by weight of alkylaryl polyglycol ether To produce a suitable preparation of active compound, 1 part by weight of herbicidal active compound or antidote, or of a mixture of antidote and herbicidal active compound, was mixed with the stated amount of solvent, the stated amount of emulsifier was added and the concentrate was diluted with water to the desired concentration.

Seeds of the test plants were sown in normal soil and, after 24 hours, watered with the herbicide preparation or antidote preparation or with the preparation of antidote and herbicidal active compound. It was expedient to keep constant the amount of water per unit area. The concentration of the active compound of the preparation was of no importance, only the amount of active compound applied per unit area being decisive. After three weeks, the degree of damage to the plants was rated in % damage in comparison to the development of the untreated control. The figures denote:

0% = no action (like untreated control)
100% = total destruction

The active compounds, amounts used and results can be seen from the table which follows:

TABLE A

| Active compound Herbicide | Pre-emergence test Amount of herbicide used as the active compound (kg/ha) | Amount of N,N-diallyl-dichloroacet-amide used as the active compound (kg/ha) | Damage, in %, to Corn | Echinochloa | Amaranthus |
|---|---|---|---|---|---|
| [structure 1: C₂H₅/C₂H₅-substituted anilide with CH₂-pyrazolyl and CO-CH₂Cl] | 3 | — | 70 | 100 | 100 |
| | 3 | 0.5 | 0 | 100 | 100 |
| [structure 2: similar C₂H₅/C₂H₅ anilide] | 3 | — | 30 | 100 | 100 |
| | 3 | 0.5 | 0 | 100 | 100 |
| [structure 3: CH₃/C₂H₅-substituted anilide] | 3 | — | 90 | 100 | 100 |
| | 3 | 0.5 | 0 | 100 | 100 |

It will be understood that the specification and examples are illustrative but not limitative of the present invention and that other embodiments within the spirit and scope of the invention will suggest themselves to those skilled in the art.

What is claimed is:

1. Herbicidal composition comprising as an active ingredient, an acetanilides of the formula

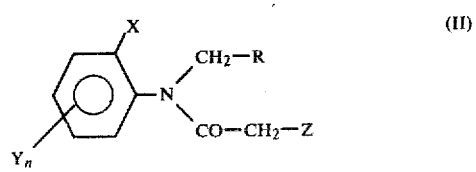

(II)

in which
R is pyrazol-1-yl or substituted pyrazol-1-yl, wherein the substituents are selected from the group consisting of halogen and alkyl of 1 to 4 carbon atoms;
X and Y, which may be identical or different, each represent straight chain or branched alkyl with 1 to 4 carbon atoms;
Z is chlorine or bromine; and
n is 0, 1 or 2 and herbicidally active acid-addition salts thereof;

and N,N-diallyl-dichloroacetamide, of the formula

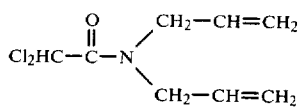

as an antidote against damage to crop plants.

2. Herbicidal compositions as claimed in claim 1 wherein in the formula (II) of said acetanilide
R is pyrazol-1-yl;
X and Y, which may be identical or different, each represent straight-chain or branched alkyl with 1 to 4 carbon atoms; and
Z represents chlorine or bromine.

3. Herbicidal composition as claimed in claim 1 containing an acetanilide of the formula (II) in the form of an addition salt of an acid selected from hydrogen halide acids, phosphoric acid, nitric acid, sulphuric acid, sulphonic acids and monofunctional or bifunctional carboxylic or hydroxycarboxylic acids.

4. Herbicidal composition as claimed in claim 1 wherein said acetanilide is the following:

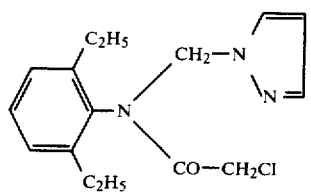

5. Herbicidal composition as claimed in claim 1 wherein said acetanilide is the following:

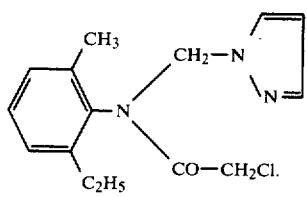

6. Herbicidal composition as claimed in claim 1 wherein said acetanilide is the following:

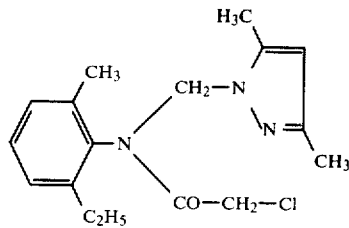

7. Herbicidal composition as claimed in claim 1 wherein said composition additionally contains a herbicidally acceptable carrier and contains from 0.1 to 95% by weight of said components (1) and (2).

8. Herbicidal composition as claimed in claim 1 containing 0.05 to 1 part by weight of the antidote component (2) per part by weight of the acetanilide component (1).

9. Herbicidal composition as claimed in claim 1 containing 0.1 to 0.5 part by weight of the antidote component (2) per part by weight of the acetanilide component (1).

10. Method of protecting crop plants against damage by a herbicidally active acetanilide compound which method comprises applying to said crop plants or their habitat N,N-diallyl-dichloroacetamide of the formula

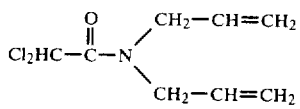

11. Method as claimed in claim 10 wherein said herbicidally active acetanilide compound is applied to an area of crop-plant cultivation at a rate of 0.1 to 5 kg per hectare and said antidote compound of formula (I) is applied at a rate of 0.1 to 5 kg per hectare.

12. Method as claimed in claim 11 wherein said herbicidally active acetanilide compound is applied to an area of crop-plant cultivation at a rate of 0.2 to 4 kg per hectare.

13. Method as claimed in claim 10 wherein said herbicidally active acetanilide compound and the antidote of compound or formula (1) are applied simultaneously.

14. Method of protecting crop plants against damage by a herbicidally active acetanilide compound of the formula

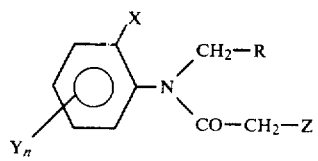

in which
R is pyrazol-1-yl or substituted pyrazol-1-yl, wherein the substituents are selected from the group consisting of halogen and alkyl of 1 to 4 carbon atoms;
X and Y, which may be identical or different, each represent straight chain or branched alkyl with 1 to 4 carbon atoms;
Z is chlorine or bromine; and
n is 0, 1 or 2
and herbicidally active acid-addition salts thereof;
by applying, as an antidote against damage to crop plants, N,N-diallyl-dichloroacetamide, of the formula

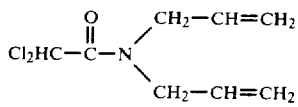

15. Method as claimed in claim 14 wherein said acetanilide compound is selected from the following:

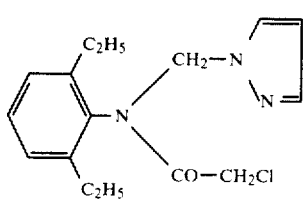

-continued
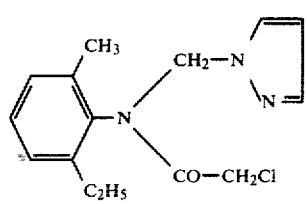
-continued
and
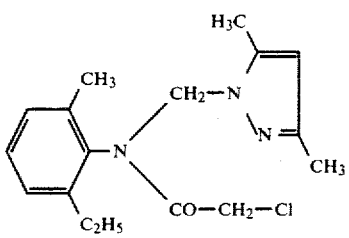
* * * * *